(12) United States Patent
Igari et al.

(10) Patent No.: US 11,339,351 B2
(45) Date of Patent: May 24, 2022

(54) METHOD FOR PRODUCING POLYHYDROXYALKANOATE

(71) Applicant: KANEKA CORPORATION, Osaka (JP)

(72) Inventors: Takafumi Igari, Takasago (JP); Wanying Lee, Batu Caves (MY); Shingo Kobayashi, Takasago (JP)

(73) Assignee: KANEKA CORPORATION, Osaka (JP)

( * ) Notice: Subject to any disclaimer, the term of this patent is extended or adjusted under 35 U.S.C. 154(b) by 3 days.

(21) Appl. No.: 17/058,932

(22) PCT Filed: May 27, 2019

(86) PCT No.: PCT/JP2019/020884
§ 371 (c)(1),
(2) Date: Nov. 25, 2020

(87) PCT Pub. No.: WO2019/230644
PCT Pub. Date: Dec. 5, 2019

(65) Prior Publication Data
US 2021/0214645 A1 Jul. 15, 2021

(30) Foreign Application Priority Data
May 30, 2018 (JP) .............................. JP2018-103862

(51) Int. Cl.
*C11C 1/10* (2006.01)
*C12P 7/625* (2022.01)

(52) U.S. Cl.
CPC ................ *C11C 1/10* (2013.01); *C12P 7/625* (2013.01)

(58) Field of Classification Search
CPC ............... C11C 1/10; C12P 7/625; C12P 7/62
See application file for complete search history.

(56) References Cited

U.S. PATENT DOCUMENTS

2018/0087076 A1   3/2018   Hayashi

FOREIGN PATENT DOCUMENTS

| EP | 2 896 701 A1 | 7/2015 |
|---|---|---|
| JP | 2000-189183 A | 7/2000 |
| WO | WO 2014/042076 A1 | 3/2014 |
| WO | WO 2016/170797 A1 | 10/2016 |

OTHER PUBLICATIONS

International Search Report dated Aug. 20, 2019 in PCT/JP2019/020884 filed on May 27, 2019, 1 page.

*Primary Examiner* — Deborah D Carr
(74) *Attorney, Agent, or Firm* — Oblon, McClelland, Maier & Neustadt, L.L.P.

(57) ABSTRACT

A free fatty acid-containing substance, which is a waste liquid or by-product obtained in a process for producing palm oil or which is a hydrolysate of the waste liquid or by-product, is subjected to distillation treatment to obtain a free fatty acid fraction satisfying the requirements (i), (ii) and (iii), and a polyhydroxyalkanoate-producing microorganism is cultured in a culture solution containing the free fatty acid fraction. (i) The content of squalene is 0.05 wt % or less. (ii) The ratio of a peak area of trimethylindene to a peak area of a naphthalene-d8 standard is 110 or less in first-dimensional dynamic headspace-GC/TOFMS analysis. (iii) The ratio of a peak area of butyric acid to a peak area of a naphthalene-d8 standard is less than 10 in first-dimensional dynamic headspace-GC/TOFMS analysis.

12 Claims, No Drawings

METHOD FOR PRODUCING POLYHYDROXYALKANOATE

TECHNICAL FIELD

The present invention relates to a method for producing polyhydroxyalkanoate by a polyhydroxyalkanoate-producing microorganism.

BACKGROUND ART

Polyhydroxyalkanoate (hereinafter, sometimes abbreviated as "PHA") is thermoplastic polyester produced and accumulated as an energy storage substance in cells of many microbial species. PHA, which is produced from various natural carbon sources by microorganisms, is completely biodegraded by microorganisms in soil and water. Therefore, PHA is incorporated into a carbon cycle process in nature. Thus, it can be said that PHA is an environmentally friendly plastic which has little negative impact on the ecosystem.

For production of PHA, a method is carried out in which a microorganism capable of producing PHA is cultured, and the PHA is taken out from the microorganism. The culture requires supply of a carbon source which is favorably consumed by the microorganism. Typical examples of the carbon source include carbohydrates, fats and oils, and free fatty acids.

For example, Patent Literature 1 describes a method for producing PHA by culturing a PHA-producing microorganism using a plant-derived free fatty acid.

Further, Patent Literature 2 describes a method for producing PHA by hydrogen bacteria using less expensive vegetable oil waste as a carbon source.

Patent Literature 3 discloses a method in which an intensely colored oil and fat such as residual oil remaining after a distillation step during production of palm oil is subjected to heating treatment with hydrogen peroxide, and a microorganism is cultured with the oil and fat as a carbon source to produce PHA.

CITATIONS LIST

Patent Literatures

PTL 1: International Publication No. WO 2014/042076
PTL 2: Japanese Patent Laid-Open Publication No. 2000-189183
PTL 3: International Publication No. WO 2016/170797

SUMMARY OF INVENTION

Technical Problem

Waste liquid or by-products obtained in a process for producing palm oil are available at a lower cost than palm oil as a general plant oil, and are environmentally advantageous as non-edible raw material sources which do not compete with food. Thus, studies have been conducted on use of the above-mentioned waste liquid or by-product as carbon sources used in culture of a PHA-producing microorganism, and resultantly, it has been found that there is a drawback that the PHA production rate is markedly low, or the resulting PHA has an odor and an unfavorable color.

In view of the above-mentioned circumstance, an object of the present invention is to provide a method for producing polyhydroxyalkanoate, which enables less odorous polyhydroxyalkanoate to be produced with good productivity by culturing polyhydroxyalkanoate-producing microorganism using a waste liquid or by-product obtained in a process for producing palm oil; and a method for producing a polyhydroxyalkanoate-producing microorganism culturing carbon source.

Solution to Problem

The present inventors have confirmed that a waste liquid or by-product obtained in a process for producing palm oil contain a component that can inhibit growth of PHA-producing microorganisms, and the inhibiting component is squalene. Further, the waste liquid or by-product obtained in a process for producing palm oil has been found to contain odorous components, and trimethylindene and butyric acid have been identified as the odorous components. The present inventors have found that by subjecting the waste liquid or by-product obtained in a process for producing palm oil, or hydrolysates thereof to a distillation step, a free fatty acid fraction having reduced contents of squalene, vitamin E, β-carotene, trimethylindene and butyric acid can be obtained, and by culturing a PHA-producing microorganism with the free fatty acid fraction used as a carbon source, less odorous PHA can be produced with good productivity.

That is, the present invention relates to a method for producing polyhydroxyalkanoate, the method including step (a) of subjecting a free fatty acid-containing substance, which is a waste liquid or by-product obtained in a process for producing palm oil or which is a hydrolysate of the waste liquid or by-product, to distillation treatment to obtain a free fatty acid fraction satisfying the following requirements (i), (ii) and (iii); and step (b) of culturing a polyhydroxyalkanoate-producing microorganism in a culture solution containing the free fatty acid fraction.

(i) The content of squalene is 0.05 wt % or less.
(ii) The ratio of a peak area of trimethylindene to a peak area of a naphthalene-d8 standard is 110 or less in first-dimensional dynamic headspace-GC/TOFMS analysis.
(iii) The ratio of a peak area of butyric acid to a peak area of a naphthalene-d8 standard is less than 10 in first-dimensional dynamic headspace-GC/TOFMS analysis.

Preferably, the free fatty acid fraction further satisfies the following requirements (iv) and (v).
(iv) The content of vitamin E is less than 0.01 wt %.
(v) The content of β-carotene is 0.001 mg/L or less.

The waste liquid may be a waste liquid which is discharged in the process of obtaining crude palm oil from oil palm fruit: POME. The by-product may be a by-product obtained in the process of obtaining RBD palm oil from crude palm oil: PFAD. The by-product may be a by-product obtained in the process of obtaining empty fruit bunch pellets from empty fruit bunch of oil palm: EFB juice, and a hydrolysate of the EFB juice may be subjected to a distillation treatment in step (a).

The distillation treatment is preferably treatment in which (i) the free fatty acid-containing substance is distilled under the conditions of 0.6 to 1.6 Torr and 175 to 185° C. to separate a bottom fraction and a top fraction, and (ii) the bottom fraction is distilled under the conditions of 0.6 to 1.6 Torr and 190 to 200° C. to obtain the free fatty acid fraction as a top fraction.

The present invention also relates to a method for producing a polyhydroxyalkanoate-producing microorganism culturing carbon source, the method including the step of subjecting a free fatty acid-containing substance, which is a waste liquid or by-product obtained in a process for producing palm oil or which is a hydrolysate of the waste liquid or by-product, to distillation treatment to obtain a free fatty acid fraction satisfying the requirements (i), (ii) and (iii).

Advantageous Effects of Invention

The method for producing polyhydroxyalkanoate according to the present invention enables less odorous polyhydroxyalkanoate to be produced with good productivity by culturing polyhydroxyalkanoate-producing microorganism using a carbon source derived from a waste liquid or by-product obtained in a process for producing palm oil.

The method for producing a polyhydroxyalkanoate-producing microorganism culturing carbon source according to the present invention can provide a carbon source which is derived from a waste liquid or by-product obtained in a process for producing palm oil and which enables less odorous polyhydroxyalkanoate to be produced with good productivity.

DESCRIPTION OF EMBODIMENTS

Hereinafter, specific embodiments of the present invention will be described in detail, but the present invention is not limited to these embodiments.

The method for producing polyhydroxyalkanoate (PHA) according to the present invention includes step (a) of subjecting a free fatty acid-containing substance, which is a waste liquid or by-product obtained in a process for producing palm oil or which is a hydrolysate of the waste liquid or by-product, to distillation treatment to obtain a free fatty acid fraction satisfying the following requirements (i), (ii) and (iii); and step (b) of culturing a PHA-producing microorganism in a culture solution containing the free fatty acid fraction.

(Step (a))

First, step (a) of preparing a free fatty acid fraction by distillation treatment will be described. In step (a), a free fatty acid-containing substance, which is a waste liquid or by-product obtained in a process for producing palm oil or which is a hydrolysate of the waste liquid or by-product, is subjected to distillation treatment.

Various kinds of the waste liquid or by-product obtained in a process for producing palm oil are known, and in the present invention, it is possible to use a waste liquid or by-product containing free fatty acids, or a waste liquid or by-product containing triglycerides in which three fatty acid molecules are bonded to one glycerol molecule. The waste liquid or by-product is not limited, and examples thereof include the following.

(i) PFAD (Palm Fatty Acid Distillate): By-product obtained in the process of obtaining RBD palm oil from crude palm oil.

(ii) POME (Palm Oil Mill Effluent): Waste liquid discharged in the process of obtaining crude palm oil from oil palm fruit.

(iii) EFB juice (Empty Fruit Bunch Juice): By-product obtained in the process of obtaining empty fruit bunch pellets from empty fruit bunches of oil palm.

An example of the process for producing palm oil will be described below, but the present invention is not limited to the example.

In the process for producing palm oil, first, afresh fruit bunch (FFB) of palm oil is subjected to a steaming step using steam, and the bunch is then peeled off to extract fruit. The extracted fruit is then subjected to the steps of digestion, screw pressing, vibration sieving, refining and vacuum drying to produce crude palm oil (CPO). The above-mentioned steps are carried out in an oil mill.

In the FFB steaming step, waste liquid containing free fatty acids, water and other solids is generated. This is POME (Palm Oil Mill Effluent). POME may contain triglycerides in addition to free fatty acids.

The empty fruit bunch (EFB) peeled from FFB is pressed, then pelletized, and can be used for biomass power generation or the like, and a liquid by-product generated in the process of pressing and pelletizing the EFB is EFB juice. EFB juice is a mixture of triglycerides and free fatty acids, and is a material richer in triglycerides than in free fatty acids.

The crude palm oil produced in the oil mill is transported to an oil refinery, where the crude palm oil is subjected to the steps of degumming, deacidification, bleaching with white clay, deodorization by distillation to produce RBD (Refined, Bleached and Deodorized) palm oil. In the distillation, free fatty acids contained in crude palm oil are removed. The by-product containing free fatty acids removed by the distillation is PFAD (Palm Fatty Acid Distillate).

In the present invention, the by-product or waste liquid described above is used as a raw material, and subjected to distillation treatment to produce a carbon source that can be suitably used in culture of a PHA-producing microorganism.

When the waste liquid or by-product contains water or solids, it is preferable to remove the water or solids by performing centrifugation before the distillation treatment. The conditions for centrifugation are not particularly limited, and can be appropriately determined in consideration of the state of the waste liquid or by-product, the type and the amount of water and solids contained in the waste liquid or by-product.

When the waste liquid or by-product is a material rich in free fatty acids (e.g. PFAD, or POME substantially free of triglycerides), the waste liquid or by-product can be centrifuged if necessary, and then subjected to distillation treatment. However, when the waste liquid or by-product is a material rich in triglycerides (e.g. EFB juice, or POME rich in triglycerides), the waste liquid or by-product can be centrifuged if necessary, then subjected to hydrolysis treatment to convert the triglycerides into free fatty acids, and then subjected to distillation treatment. Whether or not the hydrolysis treatment is to be performed may be appropriately determined in consideration of the content of triglycerides in the waste liquid or by-product. Conversion of triglycerides into free fatty acids by hydrolysis treatment facilitates separation of impurities such as colored components from the carbon source.

The hydrolysis treatment is not particularly limited as long as it is a treatment method which allows free fatty acids to be obtained by hydrolyzing triglycerides, and a known treatment method can be appropriately employed. Examples thereof include a method in which a basic substance such as sodium hydroxide is added; and a method in which an enzyme such as lipase is added.

In the present invention, the waste liquid or by-product is subjected to distillation treatment in step (a) directly or after being centrifuged and/or hydrolyzed as described above, whereby culture inhibiting components, odorous components and preferably colored components contained in material before distillation are reduced in amount or removed to obtain a free fatty acid fraction having a low content of these components.

The free fatty acids contained in the free fatty acid fraction are not particularly limited, and examples of main free fatty acids include palmitic acid and oleic acid. The free fatty acids include linoleic acid, stearic acid and myristic acid in addition to those mentioned above. The total content of palmitic acid and oleic acid in the free fatty acid fraction is preferably 50 wt % or more, more preferably 60 wt % or more, still more preferably 70 wt % or more.

The inventors of the present application have found that when a PHA-producing microorganism is cultured with PFAD used as a carbon source, the culture is inhibited, so that the PHA productivity and the carbon source yield are significantly reduced. The present inventors have conducted studies for solving this problem, and resultantly found that a component contained in PFAD inhibits production of PHA by the microorganism, and the component is squalene. PFAD intrinsically contains about 1 wt % of squalene.

On the basis of this finding, in the present invention, the content of squalene in a free fatty acid-containing substance intrinsically containing squalene at a high concentration, such as PFAD, is reduced, and the free fatty acid-containing substance is then used as a carbon source during culture of a PHA-producing microorganism. In step (a) in the present invention, the free fatty acid-containing substance is subjected to distillation treatment to obtain a free fatty acid fraction having a squalene content of 0.05 wt % or less. When the content of squalene is within this range, production of PHA by the microorganism is less likely to be inhibited, and PHA productivity and the carbon source yield can be improved. The smaller the content of squalene in the resulting free fatty acid fraction, the better. The content of squalene in the resulting free fatty acid fraction is preferably 0.04 wt % or less, more preferably 0.03 wt % or less, still more preferably 0.02 wt % or less, even more preferably 0.01 wt % or less.

When a PHA-producing microorganism is cultured using a free fatty acid-containing substance, which is a waste liquid or by-product obtained in a process for producing palm oil or which is a hydrolysate of the waste liquid or by-product, as a carbon source, the resulting PHA may have an odor, and an unpreferable color. The present inventors have conducted studies for producing odorless and uncolored PHA, and resultantly found that as substances causing an odor, trimethylindene, tetrahydrotrimethylnaphthalene, tetramethylindane and the like are contained in PFAD, and butyric acid, guaiacol, mequinol and the like are contained in POME and EFB juice. Further, it has been confirmed that as substances causing coloring, vitamin E (tocopherol and tocotrienol) is contained in PFAD, and vitamin E and β-carotene are contained in EFB juice.

On the basis of this finding, in the present invention, the content of odorous components in a free fatty acid-containing substance containing the odorous components at a high concentration is reduced, and the free fatty acid-containing substance is then used as a carbon source during culture of a PHA-producing microorganism. Specifically, in the step (a) in the present invention, the free fatty acid-containing substance is subjected to distillation treatment to obtain a free fatty acid fraction in which the ratio of a peak area of trimethylindene to a peak area of a naphthalene-d8 standard is 110 or less, and the ratio of a peak area of butyric acid to the peak area of a naphthalene-d8 standard is less than 10, in first-dimensional dynamic headspace-GC/TOFMS analysis. When the contents of trimethylindene and butyric acid are within the above-mentioned ranges, it is possible to obtain PHA whose odor is sufficiently suppressed. The peak area ratio of trimethylindene is preferably 90 or less, more preferably 70 or less. The peak area ratio of butyric acid is preferably 7 or less, more preferably 5 or less. The first-dimensional dynamic headspace-GC/TOFMS analysis can be performed by a method as described later.

For the colored components, it is preferable that the content of colored components in a free fatty acid-containing substance containing the colored components at a high concentration be reduced, and the free fatty acid-containing substance is then used as a carbon source during culture of a PHA-producing microorganism. Preferably, a free fatty acid fraction having a vitamin E content of less than 0.01 wt % and a β-carotene content of 0.001 mg/L or less is obtained by step (a) in the present invention. When the contents of vitamin E and β-carotene are within the above-mentioned ranges, it is possible to obtain PHA in which coloring is sufficiently suppressed. The content of vitamin E is preferably 0.005 wt % or less, more preferably 0.001 wt % or less. The content of β-carotene is preferably 0.0005 mg/L or less, more preferably 0.0001 mg/L or less.

The specific conditions for distillation treatment in step (a) are not particularly limited as long as the above-described various impurities can be removed by the distillation treatment, and those skilled in the art can appropriately determine the conditions in consideration of the boiling points of the impurities including squalene, odorous components and colored components. In the distillation step, it is preferable to perform vacuum distillation, and industrially, it is preferable to perform the following treatment in a distillation column as an example of vacuum distillation.

First, a free fatty acid-containing substance, which is the waste liquid or by-product or a hydrolysate thereof, is distilled under the conditions of a pressure of 0.6 to 1.6 Torr and a temperature of 175 to 185° C. (primary distillation) to be separated into a bottom fraction and a top fraction. Consequently, low-melting-point odorous components such as butyric acid and trimethylindene belong to the top fraction, and free fatty acids and high-melting-point substances belong to the bottom fraction.

The bottom fraction obtained by the primary distillation is subjected to secondary distillation. In the secondary distillation, distillation is performed under the conditions of a pressure of 0.6 to 1.6 Torr and a temperature of 190 to 200° C. to separate the fraction into a bottom fraction and a top fraction. Here, colored components including vitamin E and β-carotene and culture inhibiting components including squalene have a high melting point, and therefore remain in the bottom fraction, and free fatty acids are obtained as a top fraction from the top of the distillation column.

The pressure and temperature during distillation as described above can be appropriately changed by those skilled in the art on the basis of common knowledge about distillation. The scope of the present invention also includes distillation performed at the changed pressure and temperature.

The primary distillation and the secondary distillation may be performed sequentially in the same distillation column, but it is preferable to perform the distillations in different distillation columns for avoiding a situation in which odorous components to be removed in the primary distillation is brought to the secondary distillation. That is, it is preferable that the bottom fraction obtained by the primary distillation be transferred into another distillation column, where secondary distillation is performed. Alternatively, after through washing of the inside of the distillation column in which the primary distillation has been performed, the secondary distillation may be performed in the same distillation column.

(Step (b))

Step (b) will now be described. In step (b), the PHA-producing microorganism is cultured in a culture solution containing as a carbon source the free fatty acid fraction obtained in step (a).

The polyhydroxyalkanoate (PHA) in the present invention is not particularly limited as long as it is PHA that can be produced by a microorganism, and homopolymers of one monomer selected from 3-hydroxyalkanoates having 4 to 16 carbon atoms, copolymers of one monomer selected from 3-hydroxyalkanoates having 4 to 16 carbon atoms and other hydroxyalkanoates (e.g. 4-hydroxyalkanoates having 4 to 16 carbon atoms and lactic acid), and copolymers of two or more monomers selected from 3-hydroxyalkanoates having 4 to 16 carbon atoms are preferable. Specific examples thereof include, but are not limited to, P(3HB) as homopolymers of 3-hydroxybutyric acid (abbreviation: 3HB); copolymers of 3HB and 3-hydroxyvaleric acid (abbreviation: 3HV) (P(3HB-co-3HV)); copolymers of 3HB and 3-hydroxyhexanoic acid (abbreviation: 3HH) (P(3HB-co-3HH)) (abbreviation: PHBH)); copolymers of 3HB and 4-hydroxybutyric acid (abbreviation: 4HB) (P(3HB-co-4HB)); and copolymers of LA and PHA containing lactic acid (abbreviation: LA) as a constituent component, for example 31-B (P(LA-co-3HB)). Of these, PHBH is preferable from the viewpoint of a wide application range as a polymer. The type of PHA produced can be appropriately selected according to the type of a PHA synthase gene of a microorganism used or a PHA synthase gene introduced separately, the type of a metabolic gene involved in synthesis thereof, and culture conditions.

The PHA-producing microorganism that can be used in the present invention is not particularly limited as long as it is a PHA-producing microorganism capable of producing PHA, and the PHA-producing microorganism may be a microorganism found in nature, or a mutant or transformant. Specific examples of the PHB-producing bacterium include *Bacillus megaterium* discovered in 1925, *Cupriavidus necator* (former class name: *Alcaligenes eutrophus*), *Ralstonia eutropha* and *Alcaligenes latus*. Examples of the bacteria producing copolymers of 3-hydroxybutyrate and other hydroxyalkanoates include PHBV and PHBH producing bacteria such as *Aeromonas caviae*, and P3HB4HB producing bacteria such as *Alcaligenes eutrophus*.

In particular, examples of the PHBH-producing bacteria include the *Alcaligenes eutrophus* AC32 strain (*Alcaligenes eutrophus* AC32, FERM BP-6038) into which a PHA synthase group gene has been introduced in order to enhance PHBH productivity (T. Fukui, Y Doi, J. Bateriol, 179, p 4821-4830 (1997)).

The PHA synthase gene introduced by transformation is not particularly limited, and examples thereof include polyhydroxyalkanoate synthase genes derived from *Aeromonas caviae, Aeromonas hydrophila*, Pseuromonas SP 61-3, and *Cupriavidus necator*, and variants thereof. The variant refers to a base sequence encoding a PHA synthase having an amino acid sequence in which one or more amino acid residues are deleted, added, inserted or substituted.

By culturing the PHA-producing microorganism as described above, PHA can be accumulated in bacterial cells. In culture, the free fatty acid fraction obtained in step (a) is added to the medium as a carbon source. Preferably, the carbon source is added to the medium continuously or intermittently. The amount of the carbon source used can be appropriately set, and is, for example, about 200 to 1700 g per 10 L jar.

Since the free fatty acid fraction has a high melting point, feeding of the carbon source is likely to cause the problem that the free fatty acid fraction solidifies in a feeding line, so that the line is blocked. Even when the free fatty acid fraction is fed to the medium while being heated for avoiding the above-mentioned problem, it may be impossible to perform culture because the free fatty acid fraction solidifies to aggregate instantly when arriving at the medium. Therefore, it is preferable to employ a method in which the free fatty acid fraction is mixed with water to prepare an emulsion, and the emulsion is added to the medium, or the free fatty acid fraction is sprayed to the medium.

As the carbon source, free fatty acids having a different origin or another carbon source such as triglycerides may be used together with the free fatty acid fraction obtained in step (a).

It is possible to conform to a common microorganism culture method for culture conditions other than the carbon source, and the medium composition, culture scale, aeration and stirring conditions, culture temperature, culture time and the like are not particularly limited.

Culture is performed for an appropriate time to accumulate PHA in bacterial cells, and PHA is then recovered from the bacterial cells using a well-known method. The recovery method is not particularly limited, and for example, the following method can be used. After completion of culture, bacterial cells are separated from a culture solution by a centrifuge or the like, and the bacterial cells are washed with distilled water, methanol and the like, and dried. PHA is extracted from the dried bacterial cells using an organic solvent such as chloroform. From the solution containing PHA, bacterial cell components are removed by filtration or the like, and a poor solvent such as methanol or hexane is added to the filtrate to precipitate PHA. Further, the supernatant can be removed by filtration or centrifugation, and dried to recover PHA.

As described above, it is possible to efficiently produce less odorous and preferably less colored PHA while efficiently utilizing a waste liquid and by-product, which are obtained in a process for producing palm oil, as a carbon source.

EXAMPLES

Hereinafter, the present invention will be described in further detail byway of examples, but the present invention is not limited to these examples.

(Example 1 and Comparative Example 1) Use of PFAD

In the following experiments, PFAD obtained from FELDA through a SUS pipe so as not to contact an iron pipe was used.

(Primary Distillation) Removal of Low-Melting-Point Fraction 90 g of PFAD was added to a 200 mL flask, a connecting pipe (having a T-shape and an angle of 75°) and a condenser were connected to the flask, and the condenser was connected to a vacuum pump and a recovery container to assemble a vacuum single distillation system.

Heating was started using an oil bath while evacuation was performed under the stirring condition of 1000 rpm with stirrer. A cooling medium solution at about 4° C. was caused to pass through the condenser. At the time when the temperature of PFAD in the flask reached 175 to 185° C. at a system pressure of 0.6 to 1.6 Torr, low-melting-point odorous components including trimethylindene were distilled out, and removed through the condenser. At the start of distillation of the odorous components, the temperature of the gas phase portion in the system increased, and at the end of distillation of the odorous components, the temperature decreased. It was determined that primary distillation was completed by this temperature decrease. The residue in the flask was used in subsequent secondary distillation.

(Secondary Distillation) Removal of High-Melting-Point Fraction

The residue obtained by the primary distillation was recovered, and put into a 200 mL (or 1000 mL) flask, a Vigreux column was then connected to the flask, and the column was connected to a vacuum pump and a recovery container to additionally assemble a vacuum single distillation system. In the secondary distillation, distilled free fatty acids would be recovered, and therefore use of a condenser was avoided in order to prevent the risk of blocking the line by high-melting-point fatty acids.

Heating was started using an oil bath while evacuation was performed under the stirring condition of 1000 rpm with stirrer. At the time when the internal temperature of the flask reached 190 to 200° C. at a pressure of 0.6 to 1.6 Torr in the system, distillation of colorless free fatty acids started. Here, the temperature of the gas phase portion increased, and the temperature decreased at the time when the distillation of free fatty acids was completed. It was determined that secondary distillation was completed by this temperature decrease. In this way, a free fatty acid fraction accounting for about 80 wt % of PFAD subjected to the primary distillation was recovered.

By the secondary distillation, components higher in melting point than free fatty acids, i.e. colored components including vitamin E and β-carotene and culture inhibiting components including squalene were caused to remain in the flask, and removed from the free fatty acid fraction.

(Measurement of Contents of Impurities)

The contents of squalene, trimethylindene, butyric acid, vitamin E and β-carotene were measured in the obtained free fatty acid fraction (Example 1). In addition, the content of each component was similarly measured for PFAD (Comparative Example 1) itself before the PFAD was subjected to primary distillation. The results are shown in Table 1 below.

The content of each component was measured using the apparatuses described below.

(Measurement of Contents of Squalene and Vitamin E) Gas Chromatography (GC)

25 mg of a sample was added to a solvent (n-hexane/isopropyl alcohol=2/5 (volume ratio) mixed solution), adjusted to 50 ml with a measuring flask, and then filtered, and the thus-obtained product was subjected to GC analysis under the following conditions. According to this analysis method, the detection limit of vitamin E is 0.0001 wt %. In Table 1, "N. D." indicates that detection of vitamin E was not possible.

Analysis equipment: GC (equivalent to Shimadzu GC-2010)
Column: DB-1MS UI (5.0 m×0.25 mm ID, membrane pressure 0.25 μm)
Column temperature: The initial temperature is 70° C., the temperature rising rate during heating from 70° C. to 100° C. is 10° C./min, the temperature rising rate during heating from 100° C. to 180° C. is 15° C./min, the temperature rising rate during heating from 180° C. to 200° C. is 5° C./min, the temperature rising rate during heating from 200° C. to 340° C. is 15° C./min, and the sample is held at 340° C. for 12 min.
Detector: Hydrogen flame ionization detector (FID)
Inlet temperature: 300° C.
Detector temperature: 340° C.
Injection amount: 2 μl
Split ratio: 1/20
Gas: carrier gas He
Line speed: 50.0 cm/sec
Syringe washing solvent: n-hexane/isopropyl alcohol=2/5 (volume ratio) mixed liquid
Area measurement range: 33 minutes (Measurement of Contents of Trimethylindene and Butyric Acid) A First-Dimensional Dynamic Headspace-GC/TOFMS Analysis 5 mg of sample and 1 μL of a naphthalene-d8 internal standard (100 μg/ml hexane solution) were put into a vial, heated at 60° C. for 30 minutes (MPS-xt manufactured by GERSTEL), and then analyzed with n=2 by a first-dimensional DHS-GC/TOFMS method (GC: 7890B manufactured by Agilent Technology, MS: 7200 manufactured by Agilent Technology). The ratio of a peak area of trimethylindene or butyric acid to a peak area of naphthalene-d8 was calculated from the following calculation formula.

area ratio of trimethylindene or butyric acid=area of trimethylindene or butyric acid/area of naphthalene-$d$8/sample amount×1000

(Measurement of Content of β-Carotene) Lovibond Colorimeter Cyclohexane of reagent special grade was added to 0.5 g of a sample, and adjusted to 50 ml with a measuring flask. After filtration, the sample was subjected to analysis with a Lovibond analyzer (PFX iSeries manufactured by Lovibond). The optical path length was set to 10 mm.

From Table 1, it is apparent that the free fatty acid fraction obtained bypassing through primary distillation and secondary distillation (Example 1) has evidently smaller amounts of squalene as a culture inhibiting component, trimethylindene as an odorous component, and vitamin E and β-carotene as colored components as compared to PFAD which was not subjected to distillation treatment (Comparative Example 1).

(Evaluation of Odor of Carbon Source)

1 g of each of the free fatty acid fraction obtained by passing through primary distillation and secondary distillation (Example 1) and PFAD which had not been subjected to distillation treatment (Comparative Example 1) was put into an odorless 50 mL test tube. Five panelists sniffed these samples without knowing the contents, and evaluated the odors of the samples on the basis of the following criteria. Table 1 shows values obtained by averaging the evaluation scores given by the panelists.

(Odor Evaluation Criteria)
0: No odor
1: Slightly perceptible odor
2: Odor with a level at which what gives the odor can be determined
3: Easily perceptible odor
4: Strong odor
5: Very strong odor (Culture Experiment)

As the carbon source in culture of the microorganism, the free fatty acid fraction obtained from PFAD by passing through primary distillation and secondary distillation was used in Example 1, and PFAD which had not been subjected to distillation treatment was used in Comparative Example 1.

However, the free fatty acid fraction and PFAD (hereinafter, sometimes abbreviated simply as a carbon source)

have a high melting point, and therefore may rapidly solidify and hinder culture when added directly to a culture solution. Thus, a carbon source emulsion was prepared in advance by the following method, and the emulsion was added to a culture solution to perform culture.

In preparation of the emulsion, water was used in an amount determined so that the weight ratio of the carbon source to water was 6:4, casein sodium as an emulsifier was used in an amount of 0.5 wt % based on the weight of the carbon source, and $Na_2HPO_4 \cdot 12H_2O$ was used in an amount of 10.9 g per liter of water. As a procedure for preparing an emulsion, a carbon source heated to 60° C. was added little by little to 60° C.-water in which casein and the phosphate were dissolved, with a homogenizer operated so as not to cause phase inversion. In this way, a carbon source emulsion was prepared. When the emulsion was fed to the culture medium, an emulsion adjusted to a temperature of 60° C. was used.

The specific culture conditions areas follows.

The KNK-631 strain (see International Publication 2016/114128) was used for culture production.

The seed medium had a composition of 1 w/v % Meat-extract, 1 w/v % Bacto-Tryptone, 0.2 w/v % Yeast-extract, 0.9 w/v % $Na_2HPO_4 \cdot 12H_2O$ and 0.15 w/v % $KH_2PO_4$, and a pH of 6.8.

The preculture medium had a composition of 1 w/v % $Na_2HPO_4 \cdot 12H_2O$, 0.19 w/v % $KH_2PO_4$, 1.29 w/v % $(NH_4)_2SO_4$, 0.1 w/v % $MgSO_4 \cdot 7H_2O$, and 0.5 v/v % solution of a very small amount of metal salts (solution of 1.6 w/v % $FeCl_3 \cdot 6H_2O$, 1 w/v % $CaCl_2 \cdot 2H_2O$, 0.02 w/v % $CoCl_2 \cdot 6H_2O$, 0.016 w/v % $CuSO_4 \cdot 5H_2O$ and 0.012 w/v % $NiCl_2 \cdot 6H_2O$ in 0.1 N hydrochloric acid). As the carbon source, palm oil was collectively added at a concentration of 10 g/L.

The composition of the main culture medium had a composition of 0.385 w/v % $Na_2HPO_4 \cdot 12H_2O$, 0.067 w/v % $KH_2PO_4$, 0.291 w/v % $(NH_4)_2SO_4$, 0.1 w/v % $MgSO_4 \cdot 7H_2O$, and 0.5 v/v % solution of a very small amount of metal salts (solution of 1.6 w/v % $FeCl_3 \cdot 6H_2O$, 1 w/v % $CaCl_2 \cdot 2H_2O$, 0.02 w/v % $CoCl_2 \cdot 6H_2O$, 0.016 w/v % $CuSO_4 \cdot 5H_2O$, 0.012 w/v % $NiCl_2 \cdot 6H_2O$ in 0.1 N hydrochloric acid) and 0.05 w/v % BIOSPUREX200K (defoaming agent manufactured by Cognis Japan Ltd.).

First, a glycerol stock (50 µl) of the KNK-631 strain was inoculated in the seed culture medium (10 ml), and cultured at 30° C. for 24 hours to perform seed culture.

The obtained seed culture solution was inoculated at 1.0 v/v % in a 3 L jar fermenter (Model MDL-300 manufactured by B.E. MARUBISHI CO., LTD.) containing 1.8 L of the preculture medium. The operation conditions were set to a culture temperature of 30° C., a stirring speed of 600 rpm and an aeration rate of 1.8 L/min, and culture was performed for 24 hours while the pH was controlled to be 6.5. In this way, preculture was performed. A 14% ammonium hydroxide aqueous solution was used for control of pH.

Next, the obtained preculture solution was inoculated at 1.0 v/v % in a 10 L jar fermenter (Model MDS-1000 manufactured by B.E. MARUBISHI CO., LTD.) containing 6 L of the production medium. The operation conditions were set to a culture temperature of 34° C., a stirring speed of 600 rpm and an aeration rate of 6.0 L/min, and the pH was controlled to be 6.5. A 14% ammonium hydroxide aqueous solution was used for control of pH. An emulsion of the carbon source was fed while the concentration of the carbon source in the culture solution was controlled. The phosphoric acid solution was fed at a constant rate during the culture. The culture was performed for 48 hours, and after the culture was completed, bacterial cells were recovered by centrifugation, washed with methanol, and freeze-dried, and the weight of dry bacterial cells was measured.

100 ml of chloroform was added to 1 g of the obtained dry bacterial cells, the mixture was stirred at room temperature for 24 hours, and PHBH in the bacterial cells was extracted. The bacterial cell residue was separated by filtration, and concentrated with an evaporator until the total volume was 30 ml, 90 ml of hexane was then gradually added, and the mixture was left standing for 1 hour while being slowly stirred. The precipitated PHBH was separated by filtration, and then dried in vacuum at 50° C. for 3 hours to obtain PHBH. Table 1 shows PHBH productivity and carbon source yields. The PHBH productivity is a yield of PHBH per volume of culture solution (g/L), and the yield of the carbon source is a yield of PHBH per weight of carbon source supplied (g/g).

(PHBH Evaluation)

The odor and the color tone of the obtained PHBH were evaluated by the following methods. The evaluation results are shown in Table 1.

(Evaluation of Odor of PHBH)

1 g of PHBH obtained in each of examples and comparative examples was put into an odorless 50 mL test tube. Five panelists sniffed these samples without knowing the contents, and evaluated the odors of the samples on the basis of the following criteria. Table 1 shows values obtained by averaging the evaluation scores given by the panelists.

(Odor Evaluation Criteria)

0: No odor

1: Slightly perceptible odor

2: Odor with a level at which what gives the odor can be determined

3: Easily perceptible odor

4: Strong odor

5: Very strong odor (Evaluation of Color Tone)

The color tone (YI value) was measured as follows. A press sheet of the obtained PHBH was prepared and the YI value thereof was measured. The press sheet of PHBH was prepared by a method in which 3.0 g of dried PHBH was sandwiched between metal plates of 15 cm square, a 0.5 mm-thick metal plate was inserted at each of the four corners of the metal plate, the sandwiched PHBH was set in a small pressing machine for laboratory use (Model H-15 manufactured by Takabayashi Rika K.K.), heated at 160° C. for 7 minutes, then pressed at about 5 Mps for 2 minutes with heating, and then left standing at room temperature to harden the PHBH. The press sheet was placed using a 30 mm-measurement plate, and covered with a white standard plate. In this state, the YI value was measured with a color difference meter "SE-2000" (manufactured by Nippon Denshoku Industries Co., Ltd.).

TABLE 1

|  |  | Comparative Example 1 | Example 1 | Comparative Example 2 | Example 2 | Comparative Example 3 | Example 3 |
|---|---|---|---|---|---|---|---|
|  |  | PFAD | | POME | | EFB juice | |
|  | Carbon source | No distillation | After distillation | No distillation | After distillation | No distillation | After distillation |
| Content of inhibiting components in carbon source | Squalene (wt %) | 1.00 | 0.05 | 0.03 | 0.02 | 0.11 | 0.04 |
| Content of odorous components in carbon source | Trimethylindene (area %) | 1100 | 110 | 0 | 0 | 0 | 0 |
|  | Butyric acid (area %) | 0 | 0 | 280 | <10 | 15,000 | <10 |
| Content of colored components in carbon source | Vitamin E (wt %) | 0.013 | N.D. | 0.014 | N.D. | 0.026 | N.D. |
|  | β-carotin (mg/L) | 0.183 | 0.001 | 2.139 | 0.001 | 38.455 | 0.001 |
| Evaluation of carbon source | Odor (sensory evaluation) | 4 | 1.2 | 5 | 1.2 | 5 | 1.2 |
| Culture results | PHBH productivity (g/L) | 208 | 248 | — | 209 | — | 240 |
|  | Carbon source yield (g/g) | 0.95 | 1.00 | — | 1.07 | — | 1.00 |
| Evaluation of PHBH | Odor (sensory evaluation) | 3.8 | 1.2 | — | 1.2 | — | 1.2 |
|  | Color tone (YI value) | 41 | 19 | — | 18 | — | 19 |

(Example 2 and Comparative Example 2) Use of POME

In the following experiments, POME obtained from FELDA was used. The oil and fat components of POME used here were substantially composed of free fatty acids and were substantially free of triglycerides.

(Centrifugation)

First, moisture and solids contained in POME were removed, and centrifugation was performed for recovering liquid organic components including free fatty acids. For the centrifugation, 150 mL of POME melted by heating to about 50° C. was put into a 200 mL centrifuge tube, and centrifuged at room temperature using a centrifugal machine (rotar 4250 manufactured by Beckman Coulter K.K.). The centrifugation was performed at 4500 rpm for 10 minutes. Through this treatment, POM was separated into three fractions. The uppermost free fatty acid-containing fraction was recovered, and used for subsequent distillation treatment.

(Primary Distillation) Removal of Low-Melting-Point Fraction

Using a POME-derived free fatty acid-containing fraction obtained by centrifugation instead of PFAD of Example 1, primary distillation was performed under the same conditions as in Example 1.

At the time when the temperature of the free fatty acid-containing fraction in the flask reached 175 to 185° C. at a system pressure of 0.6 to 1.6 Torr, low-melting-point odorous components including butyric acid, valeric acid and caproic acid were distilled out, and removed through the condenser. At the start of distillation of the odorous components, the temperature of the gas phase portion in the system increased, and at the end of distillation of the odorous components, the temperature decreased. It was determined that primary distillation was completed by this temperature decrease. The residue in the flask was used in subsequent secondary distillation.

(Secondary Distillation) Removal of High-Melting-Point Fraction

The residue obtained in the primary distillation was recovered, and secondary distillation was performed under the same conditions as in Example 1. At the time when the internal temperature of the flask reached 190 to 200° C. at a pressure of 0.6 to 1.6 Torr in the system, distillation of colorless free fatty acids started. Here, the temperature of the gas phase portion increased, and the temperature decreased at the time when the distillation of free fatty acids was completed. It was determined that secondary distillation was completed by this temperature decrease. In this way, a free fatty acid fraction accounting for about 80 wt % of the POW-derived free fatty acid-containing fraction subjected to the primary distillation was recovered.

By the secondary distillation, components higher in melting point than free fatty acids, i.e. colored components including vitamin E and β-carotene were caused to remain in the flask, and removed from the free fatty acid fraction.

(Measurement of Contents of Impurities)

For each of the obtained free fatty acid fraction (Example 2) and the POME-derived free fatty acid-containing fraction (Comparative Example 2) before the fraction was subjected to the primary distillation, the contents of squalene, trimethylindene, butyric acid, vitamin E, and β-carotene were measured in the same manner as in Example 1. The results are shown in Table 1.

(Culture Experiment and Evaluation of PHBH)

In Example 2, PHBH was isolated by culturing a microorganism under the same conditions as in Example 1 except that a free fatty acid fraction obtained by passing through primary distillation and secondary distillation was used as a carbon source in culture of the microorganism. In the same manner as in Example 1, the odor of the carbon source was evaluated, PHBH productivity and the carbon source yield were measured, and the odor and the color tone were evaluated. The evaluation results are shown in Table 1.

Although a culture experiment using as a carbon source the POME-derived free fatty acid-containing fraction before the fraction was subjected to the primary distillation was not performed, this POME-derived free fatty acid-containing fraction contains considerable amounts of odorous components and coloring components, and therefore, when PHBH is produced using this fraction as a carbon source, insufficient results may be obtained in terms of odor and color for the PHBH as a matter of course.

(Example 3 and Comparative Example 3) Use of EFB Juice

In the following experiments, EFB juice from Dengkil was used.

(Centrifugation)

First, centrifugation was performed for recovering triglycerides by removing moisture and solids contained in EFB juice. The centrifugation was performed under the same conditions as in Example 2. Through the centrifugation treatment, the EFB juice was separated into three fractions. The uppermost triglyceride-containing fraction was recovered, and used for subsequent enzyme treatment.

(Enzyme Treatment)

Next, enzyme treatment was performed for converting triglycerides into free fatty acids. First, 45 g of an EFB juice-derived triglyceride-containing fraction obtained by centrifugation and 45 g of water were put into a 200 ml mini jar, and stirred at 40° C. at a rotation speed of 300 rpm. An enzyme (lipase manufactured by Meito Sangyo Co., Ltd.) was added to the mixture in an amount of 0.06 wt % based on the amount of triglycerides, and a hydrolysis reaction was carried out under the conditions of 40° C. and 300 rpm. The reaction time was about 60 minutes.

The solution after the enzyme treatment was recovered, and left standing at 60° C. to separate the oil layer and the aqueous layer, followed by recovering the oil layer. The obtained oil layer was melted again at 60° C., centrifuged, and the upper fatty acid-containing fraction was recovered, and used for subsequent distillation treatment.

(Primary Distillation) Removal of Low-Melting-Point Fraction

Using an EFB juice-derived free fatty acid-containing fraction obtained by the enzyme treatment instead of PFAD of Example 1, primary distillation was performed under the same conditions as in Example 1.

At the time when the temperature of the free fatty acid-containing fraction in the flask reached 175 to 185° C. at a system pressure of 0.6 to 1.6 Torr, low-melting-point odorous components including butyric acid, guaiacol, mequinol and acetic acid were distilled out, and removed through the condenser. At the start of distillation of the odorous components, the temperature of the gas phase portion in the system increased, and at the end of distillation of the odorous components, the temperature decreased. It was determined that primary distillation was completed by this temperature decrease. The residue in the flask was used in subsequent secondary distillation.

(Secondary Distillation) Removal of High-Melting-Point Fraction

The residue obtained in the primary distillation was recovered, and secondary distillation was performed under the same conditions as in Example 1. At the time when the internal temperature of the flask reached 190 to 200° C. at a pressure of 0.6 to 1.6 Torr in the system, distillation of colorless free fatty acids started. Here, the temperature of the gas phase portion increased, and the temperature decreased at the time when the distillation of free fatty acids was completed. It was determined that secondary distillation was completed by this temperature decrease. In this way, a free fatty acid fraction accounting for about 20 wt % of the EFB juice-derived free fatty acid-containing fraction subjected to the primary distillation was recovered.

By the secondary distillation, components higher in melting point than free fatty acids, i.e. colored components including vitamin E and β-carotene were caused to remain in the flask, and removed from the free fatty acid fraction.

(Measurement of Contents of Impurities)

For each of the obtained free fatty acid fraction (Example 3) and the EFB juice-derived free fatty acid-containing fraction (Comparative Example 3) before the fraction was subjected to the primary distillation, the contents of squalene, trimethylindene, butyric acid, vitamin E, and β-carotene were measured in the same manner as in Example 1. The results are shown in Table 1.

(Culture Experiment)

In Example 3, PHBH was isolated by culturing a microorganism under the same conditions as in Example 1 except that a free fatty acid fraction obtained by passing through enzyme treatment, primary distillation and secondary distillation of an EFB juice-derived triglyceride-containing fraction was used as a carbon source in culture of the microorganism. In the same manner as in Example 1, the odor of the carbon source was evaluated, PHBH productivity and the carbon source yield were measured, and the odor and the color tone were evaluated. The evaluation results are shown in Table 1.

Although a culture experiment using as a carbon source the EFB juice-derived free fatty acid-containing fraction before the fraction was subjected to the primary distillation was not performed, this EFB juice-derived free fatty acid-containing fraction contains considerable amounts of odorous components and coloring components, and therefore, when PHBH is produced using this fraction as a carbon source, insufficient results may be obtained in terms of odor and color for the PHBH as a matter of course.

(Reference Example) Experiment for Demonstrating Impacts of Squalene on Culture

PHBH was isolated by culturing a microorganism in the same manner as in Example 1 except that RBD palm oil supplemented with squalene in an amount of 1 wt % or RBD palm oil free of squalene was used as a carbon source. Table 2 shows the results of measuring the PHBH productivity and the carbon source yield in the same manner as in Example 1.

The content of squalene intrinsically contained in RBD palm oil is about 0.05 wt %, and it can be said that RBD palm oil is substantially free of squalene. In Reference Example, the amount of squalene added was 1 wt %, and this value is equivalent to the content of squalene contained in untreated PFAD.

TABLE 2

| Carbon source | PHBH Productivity (g/L) | Carbon source yield (g/g) |
|---|---|---|
| Palm oil free of squalene | 268 | 1.12 |
| Palm oil containing squalene | 209 | 1.06 |

The above results show that when the carbon source contains squalene in an amount of 1 wt %, the PHBH productivity decreases by about 22%, and the carbon source yield decreases by about 5%.

This reveals that squalene has inhibitory action on production of PHBH by PHBH-producing microorganisms.

Thus, it is evident that when a material intrinsically containing squalene, such as PFAD, is used as a carbon source, it is necessary that the material be used for culture after removal of squalene from the material.

The invention claimed is:

1. A method for producing polyhydroxyalkanoate, the method comprising:
   (a) subjecting a substance comprising a free fatty acid to distillation treatment, thereby obtaining a free fatty acid fraction comprising the free fatty acid; and
   (b) culturing a polyhydroxyalkanoate-producing microorganism in a culture solution containing the free fatty acid fraction,
   wherein the substance comprising the free fatty acid is a waste liquid or by-product obtained in a process for producing palm oil, or a hydrolysate of the waste liquid or the by-product, and
   the distillation treatment in (a) is conducted such that the free fatty acid fraction satisfies (i), (ii), and (iii):
   (i) a content of squalene is 0.05 wt % or less;
   (ii) a ratio of a peak area of trimethylindene to a peak area of a naphthalene-d8 standard is 110 or less in first-dimensional dynamic headspace-GC/TOFMS analysis; and
   (iii) a ratio of a peak area of butyric acid to a peak area of a naphthalene-d8 standard is less than 10 in first-dimensional dynamic headspace-GC/TOFMS analysis.

2. The method according to claim 1, wherein the distillation treatment in (a) is conducted such that the free fatty acid fraction further satisfies (iv) and (v):
   (iv) a content of vitamin E is less than 0.01 wt %; and
   (v) a content of β-carotene is 0.001 mg/L or less.

3. The method according to claim 1, wherein the waste liquid is palm oil mill effluent (POME).

4. The method according to claim 1, wherein the by-product is palm fatty acid distillate (PFAD).

5. The method according to claim 1,
   wherein the by-product is empty fruit bunch (EFB) juice, and
   a hydrolysate of the EFB juice is subjected to the distillation treatment in (a).

6. The method according to claim 1,
   wherein the distillation treatment comprises distilling the substance comprising the free fatty acid under conditions of 0.6 to 1.6 Torr and 175 to 185° C. to separate a bottom fraction and a top fraction, and then distilling the bottom fraction under conditions of 0.6 to 1.6 Torr and 190 to 200° C. to obtain the free fatty acid fraction as a top fraction.

7. A method for producing a carbon source suitable for culturing a polyhydroxyalkanoate-producing microorganism, the method comprising:
   subjecting a substance comprising a free fatty acid to distillation treatment, thereby obtaining a free fatty acid fraction comprising the free fatty acid,
   wherein the substance comprising the free fatty acid is a waste liquid or by-product obtained in a process for producing palm oil, or a hydrolysate thereof, and
   the distillation treatment is conducted such that the free fatty acid fraction satisfies (i), (ii), and (iii):
   (i) a content of squalene is 0.05 wt % or less;
   (ii) a ratio of a peak area of trimethylindene to a peak area of a naphthalene-d8 standard is 110 or less in first-dimensional dynamic headspace-GC/TOFMS analysis; and
   (iii) a ratio of a peak area of butyric acid to a peak area of a naphthalene-d8 standard is less than 10 in first-dimensional dynamic headspace-GC/TOFMS analysis.

8. The method according to claim 1, further comprising, prior to (a):
   removing water and a solid contained in the substance comprising the free fatty acid by centrifugation.

9. The method according to claim 1, wherein the free fatty acid comprises at least one selected from the group consisting of palmitic acid, oleic acid, linoleic acid, stearic acid and myristic acid.

10. The method according to claim 6, wherein the distillation under the conditions of 0.6 to 1.6 Torr and 175 to 185° C. and the distillation under the conditions of 0.6 to 1.6 Torr and 190 to 200° C. are carried out in different distillation columns.

11. The method according to claim 1, wherein the polyhydroxyalkanoate comprises a copolymer of 3-hydroxybutyric acid and 3-hydroxyhexanoic acid.

12. The method according to claim 1, further comprising, after (b):
   collecting the polyhydroxyalkanoate accumulated in cells of the polyhydroxyalkanoate-producing microorganism.

* * * * *